(12) United States Patent
Biskup et al.

(10) Patent No.: US 9,024,057 B2
(45) Date of Patent: May 5, 2015

(54) PROCESS FOR THE PREPARATION OF ISOCYANATES IN THE GAS PHASE

(75) Inventors: Klaus Biskup, Buichholz (DE); Rainer Bruns, Leverkusen (DE); Wolfgang Lorenz, Dormagen (DE); Fritz Pohl, Brunsbuttel (DE); Friedhelm Steffens, Leverkusen (DE); Volker Michele, Cologne (DE)

(73) Assignee: Bayer MaterialScience AG, Leverkusen (DE)

( * ) Notice: Subject to any disclaimer, the term of this patent is extended or adjusted under 35 U.S.C. 154(b) by 0 days.

(21) Appl. No.: 12/632,117

(22) Filed: Dec. 7, 2009

(65) Prior Publication Data

US 2010/0152484 A1    Jun. 17, 2010

(30) Foreign Application Priority Data

Dec. 11, 2008  (DE) .......................... 10 2008 061 686

(51) Int. Cl.
  *C07C 263/00* (2006.01)
  *C07C 263/10* (2006.01)

(52) U.S. Cl.
  CPC .................................... *C07C 263/10* (2013.01)

(58) Field of Classification Search
  CPC ............................. C07C 263/10; C07C 265/12
  See application file for complete search history.

(56) References Cited

U.S. PATENT DOCUMENTS

| 4,847,408 A | 7/1989 | Frosch et al. |
| 5,391,683 A * | 2/1995 | Joulak et al. .................... 528/67 |
| 5,449,818 A | 9/1995 | Biskup et al. |
| 5,679,839 A | 10/1997 | Armand et al. |
| 6,803,482 B2 | 10/2004 | Jenne et al. |
| 6,838,578 B2 | 1/2005 | Leimkühler et al. |
| 6,930,199 B2 | 8/2005 | Meyn et al. |
| 6,974,880 B2 | 12/2005 | Biskup et al. |
| 2005/0113601 A1 | 5/2005 | Herold et al. |
| 2009/0221846 A1* | 9/2009 | Wolfert et al. ................ 560/347 |

FOREIGN PATENT DOCUMENTS

| WO | 2007028715 A1 | 3/2007 |
| WO | 2008055898 A1 | 5/2008 |

* cited by examiner

*Primary Examiner* — Rosalynd Keys
*Assistant Examiner* — Jennifer C Sawyer
(74) *Attorney, Agent, or Firm* — Donald R. Palladino; Lyndanne M. Whalen

(57) ABSTRACT

Aromatic isocyanates are produced by reacting one or more aromatic primary amines with phosgene in the gas phase. The phosgene and primary aromatic amine(s) are reacted at a temperature above the boiling temperature of the amine(s) in a reactor having a reaction space which is essentially rotationally symmetric to the direction of flow. The flow fate, averaged over the cross-section, of the reaction mixture along the axis of the essentially rotationally symmetric reaction space in the section of the reaction space in which the conversion of the amine groups into isocyanate groups is between 4 and 80% is not more than 8 m/sec. The flow rate averaged over the cross-section of the reaction mixture along the axis of the essentially rotationally symmetric reaction space in the section of the reaction space in which the conversion of the amine groups into isocyanate groups is 4 to 80% is always below the flow rate averaged over the cross-section at the start of this section.

14 Claims, 1 Drawing Sheet

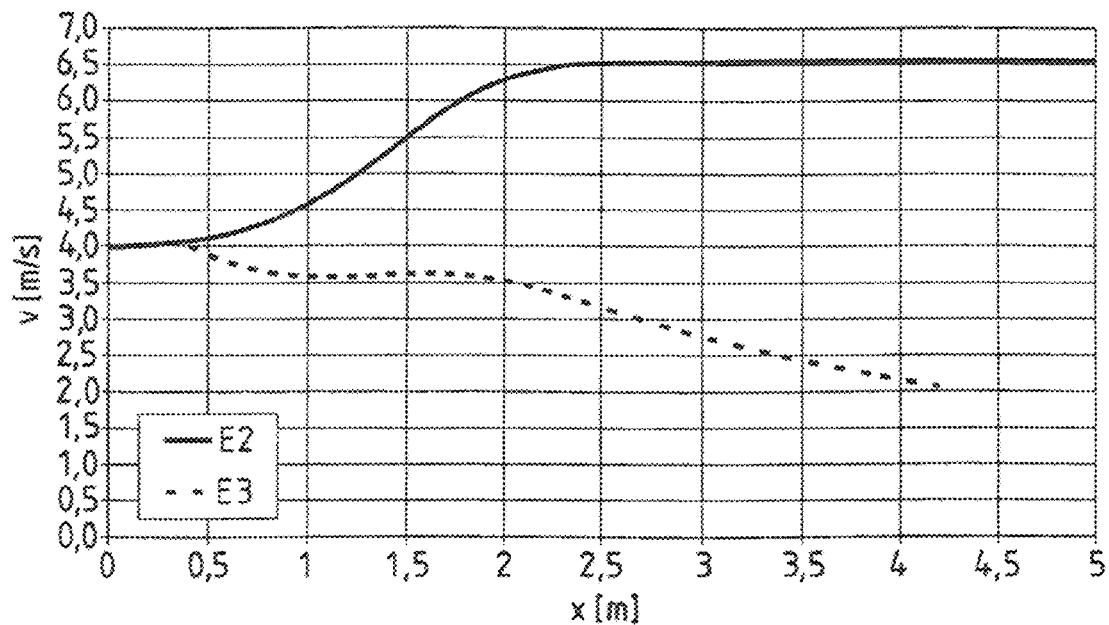

PROCESS FOR THE PREPARATION OF ISOCYANATES IN THE GAS PHASE

BACKGROUND OF THE INVENTION

The present invention relates to a gas phase process for the preparation of aromatic isocyanates by reaction of corresponding primary amines with phosgene. In this process, phosgene and one or more primary aromatic amines are reacted above the boiling temperature of the amine(s) in a reactor having a reaction space which is essentially rotationally symmetric to the direction of flow. The flow rate, averaged over the cross-section, of the reaction mixture along the axis of the essentially rotationally symmetric reaction space in the section of the reaction space in which the conversion of the amine groups into isocyanate groups is between 4 and 80% is not more than 8 m/sec. The flow rate, averaged over the cross-section, of the reaction mixture along the axis of the essentially rotationally symmetric reaction space in this section of the reaction space is always below the flow rate averaged over the cross-section at the start of this section.

Isocyanates are prepared in large amounts and serve chiefly as starting materials for the preparation of polyurethanes. They are usually prepared by reaction of the corresponding amine(s) with phosgene. One possible method for preparing isocyanates is reaction of the amine(s) with the phosgene in the gas phase. This process, which is conventionally called gas phase phosgenation, is distinguished in that the reaction conditions are chosen such that at least the reaction components (i.e., amine, isocyanate and phosgene), but preferably all the educts, products and reaction intermediate products, are gaseous under the conditions chosen. Advantages of gas phase phosgenation include a reduced phosgene hold-up, the avoidance of intermediate products which are difficult to phosgenate and increased reaction yields. The present invention relates exclusively to gas phase phosgenation.

Various processes for the preparation of isocyanates by reaction of one or more amines with phosgene in the gas phase are known from the prior art.

EP-A-289 840 describes preparation of diisocyanates by gas phase phosgenation in which a turbulent flow at temperatures of between 200° C. and 600° C. in a cylindrical space without moving parts is employed. By dispensing with moving parts, the risk of discharge of phosgene is reduced. According to the teaching of EP-A-289 840, for it to be possible to carry out the process disclosed in EP-A-289 840, it is essential for the dimensions of the tube, reactor and the flow rates in the reaction space to be such that a turbulent flow which is characterized by a Reynolds number of at least 2,500, preferably at least 4,700 prevails in the reaction space. According to the teaching of EP-A-289 840, this turbulence is in general ensured if the gaseous reaction partners pass through the reaction space with a flow rate of more than 90 m/s. Due to the turbulent flow in the cylindrical space (tube), disregarding fluid elements close to the wall, a relatively good flow equipartition in the tube and therefore a relatively narrow dwell time distribution is achieved, which, as described in EP-A-570 799, leads to a reduction in the formation of solids. A disadvantage of the process disclosed in EP-A-289 840 is that because of the necessary high flow rates, realization of the dwell time necessary for complete reaction of the amines, especially if aromatic amines are employed, is possible only in very long mixing and reactor tubes.

EP-A-570 799 discloses a process for the preparation of aromatic diisocyanates in which the reaction of the associated diamine with the phosgene is carried out in a tube reactor above the boiling temperature of the diamine within an average contact time of from 0.5 to 5 seconds. As described in the specification, reaction times which are too long and also those which are too short lead to an undesirable formation of solids. A process is therefore disclosed in which the average deviation from the average contact time is less than 6%. Maintenance of this contact time is achieved by carrying out the reaction in a tubular flow which is characterized either by a Reynolds number of above 4,000 or by a Bodenstein number of above 100. If the tubular flow is characterized by a Reynolds number above 4000, it is also a disadvantage because high flow rates make realization of the dwell time necessary for complete reaction of the amines possible only in very long mixing and reactor tubes. According to the teaching of EP-A-570 799, the approximately ideal plug flow characterized by a Bodenstein number of at least 100 can also be realized by use of installed elements in the reaction tube which counteract the formation of a laminar flow profile and have the effect of the formation of an even flow front, installed elements in the form of a three-dimensional fine-mesh wire grid or packing bodies are disclosed. A disadvantage of these process variants is that due to the installed elements, the risk of formation of deposits in the reaction tube is increased. These deposits can lead to blockages and/or inhomogeneities in the approximately ideal plug flow sought.

EP-A-699 657 describes a process for the preparation of aromatic diisocyanates in the gas phase in which the reaction of the associated diamine with the phosgene takes place in a reactor made up of two zones. The first zone, which makes up about 20% to 80% of the total reactor volume, is mixed ideally. The second zone, which makes up 80% to 20% of the total reactor volume, can be characterized by a piston flow. The second reaction zone is preferably designed as a tube reactor. However, because at least 20% of the reaction volume is back-mixed in an ideal manner, a non-uniform dwell time distribution results, which can lead to ah undesirable increased formation of solids.

Optimization of the use of tube reactors for gas phase phosgenation (as disclosed, e.g., in EP-A-570 799) using the jet mixer principle (Chemie-Ing.-Techn. 44 (1972) p. 1055, FIG. 10) is the subject matter of numerous applications.

EP-A-1 362,847 teaches that equalizing the educt stream fed via the annular space of the tube reactor and feeding of the two educt streams as centrally as possible into the tube reactor has a great positive influence on the stability of the reaction zone and therefore on the gas phase reaction overall. As a consequence of the more stable reaction procedure, the observed temperature variations decrease significantly and the asymmetry in the temperature distribution observed without the measures disclosed therein disappears almost completely. EP-A-1 362 847 also teaches that temperature variations and asymmetries in the temperature distribution lead to the formation of by-products, which lead to caking and blockages in the reactor and therefore to a shortening of the service life of the reactors. However, specific indications for conversion of the process disclosed into an industrial scale are not disclosed in EP-A-1 362 847.

As described in EP-A-1 555 258, if the tube reactors employed are increased in size, an increase in the size of the mixing nozzle, which is often constructed as a smooth jet nozzle, is also necessary. As the diameter of the smooth jet nozzle increases in size, however, the speed of mixing of the central jet is also reduced due to the longer diffusion path required, and the risk of back-mixing is increased, which in turn leads to the formation of polymeric impurities and therefore solid caking in the reactor. According to the teaching of EP-A-1 555 258, the disadvantages described can be eliminated if the one educt stream is injected at a high speed via an annular gap located concentrically in the stream of the other educt. As a result, the diffusion path for the mixing is small and the mixing times are very short. The reaction can then proceed with a high selectivity to the desired isocyanate. The formation of polymeric impurities and the development of caking are thereby reduced. EP-A-1 55 258 also teaches that use of comparable speeds of the components at the mixing point has the result that significantly shorter reaction spaces are required to achieve the maximum temperature in the reaction system than when conventional smooth jet nozzles are employed.

According to EP-A-1 526129, an increase in the turbulence of the educt stream in the central nozzle has a positive influence on the mixing of the reactants and therefore on the gas phase reaction overall. As a consequence of the better mixing, the tendency towards the formation of by-products decreases and the dwell time required and therefore reactor construction lengths drop significantly. EP-A-1 526129 teaches that the mixing zone may be shortened to 42% of the original length if a spiral coil is employed as a turbulence-generating installed element in the central nozzle.

EP-A-1 449 826 discloses a process for the preparation of diisocyanates by phosgenation of the corresponding diamines, in which the vaporous diamines, optionally diluted with an inert gas or with the vapors of an inert solvent, and phosgene are heated separately to temperatures of from 200° C. to 600° C. and are mixed and reacted in a tube reactor. In this process, a number n≥2 of nozzles aligned parallel to the axis of the tube reactor are arranged in the tube reactor, the stream containing the diamines is fed to the tube reactor via the n nozzles and the phosgene stream is fed to the tube reactor via the remaining free space. According to EP-A-1 449 826, advantages of this process include a shortening of the mixing times compared with a single nozzle (individual nozzle) with the same cross-sectional area and associated with this a shortening of the dwell time required in the reactor (investment costs advantage).

A further development of the use of tube reactors for gas phase phosgenation such as has been disclosed in EP-A-570 799 using the jet mixer principle (Chemie-Ing.-Techn. 44 (1972) p. 1055, FIG. 10) is the subject matter of WO2007/028715. WO2007/028715 discloses a process for the preparation of isocyanates by phosgenation of the corresponding amines in the gas phase in a reactor having a mixing device and a reaction space. According to WO2007/028715, the reaction space includes in the front region the mixing space in which mixing of the gaseous educts phosgene and amine, optionally mixed with an inert medium, predominantly takes place which mixing, as a rule, is accompanied by the start of the reaction. According to WO2007/028715, essentially only the reaction and at most to a minor extent the mixing then takes place in the rear region of the reaction space. Preferably, in the process disclosed in WO2007/028715, reaction spaces which are rotationally symmetric to the direction of flow and which can be broken down in construction terms essentially into up to four longitudinal sections along the longitudinal axis of the reactor in the course of flow are employed. The longitudinal sections differ in the size of the flowed-through cross-sectional area. A disadvantage of the process disclosed is the high flow rate of from 10 to 300 m/s, preferably from 40 to 230, more preferably from 50 to 200, even more preferably, from more than 150 up to 190 and most preferably from 160 to 180 m/s, with which the gaseous reaction mixture passes through the reaction space. As already described in EP-A-570 799, because of the high flow rates, realization of the dwell time necessary for complete reaction of the amines, especially if aromatic primary amines are employed, is possible only in very long reactor tubes. Another disadvantage is that the changes in the flowed-through cross-sectional area of the reaction space are generated by a volume body in a tube reactor, and the conversion of the reactor construction disclosed into an industrial scale is therefore expensive in construction terms. It is furthermore a disadvantage of volume bodies in tube reactors that, like the installed elements according to the teaching of EP-A-570 799, these increase the risk of the formation of deposits in the reaction tube, which lead to blockages and therefore to a shortened service life of the reactors.

WO2008/055898 discloses a process for the preparation of isocyanates by phosgenation of the corresponding amines in the gas phase in a reactor, in which (analogously to WO2007/028715) the reactor employed has a mixing device and a reaction space, and the rotationally symmetric reaction space can be broken down in construction terms into up to four longitudinal sections along the longitudinal axis of the reactor in the course of the flow, the longitudinal sections differing in the size of the flowed-through cross-sectional area. Compared with WO2007/028715, however, the changes in the flowed-through cross-sectional areas are achieved not by a volume body installed in a tube reactor but by a corresponding widening or constriction of the outer wall of the reactor. A disadvantage of the disclosed process is the high flow rate of from 10 to 300 m/s, preferably from 40 to 230, more preferably from 50 to 200, even more preferably from more than 150 to 190 and most preferably from 160 to 180 m/s, with which the gaseous reaction mixture passes through the reaction space, according to the teaching of WO2008/055898 in sections of the same or increasing area with area being chosen so that the average speed of the reaction mixture is in general greater than 60 m/s. The process disclosed in WO2008/055 898 indeed avoids volume adjusting components in the reaction space and therefore reduces the risk of the formation of deposits compared with the process disclosed in WO2007/028 715, but the disadvantage of the high flow rate remains. Because of the high flow rates, realization of the dwell time necessary for complete reaction of the amines, especially if aromatic primary amines are employed, is possible only in very long reaction spaces.

EP-A-1 275 639 also discloses a process for the preparation of isocyanates by phosgenation of the corresponding amines with phosgene in the gas phase using a reactor in which the reaction space has a widening of the flowed-through cross-sectional area in the direction of flow after the mixing of the two educts. According to the teaching of EP-A-1 275 639, this widening of the flowed-through cross-sectional area can be sudden, and the reaction space of the reactors employed in the process disclosed can also have a cascade-like and/or continuous change in the flowed-through cross-sectional area. According to the teaching of EP-A-1 275 639, if a cascade-like and/or continuous change is employed, the course of the speed of the reaction mixture along the axis of the reactor can be adjusted. According to EP-A-1 275 639, a narrowing of the cross-section or preferably a slight widening up to twice, preferably up to 1.5 times the starting cross-section leads to an acceleration of the flow during the reaction because of the increase in volume, which stabilizes the flow and counteracts the risk of back-flows. By a suitably chosen widening of the cross-sectional area, the flow fate of the reaction mixture can be kept just constant over the length of the reactor. As a result, the reaction time available increases for a constant length of the reactor.

SUMMARY OF THE INVENTION

It has now been found that preparation of aromatic isocyanates by phosgenation of the corresponding amines with phosgene in the gas phase is possible in reactors with a reaction space which is essentially rotationally symmetric to the direction of flow if (a) the flow rate, averaged over the cross-section, of the reaction mixture along the axis of the essentially rotationally symmetric reaction space in the section of the reaction space in which the conversion of the amine groups into isocyanate groups is between 4 and 80% is not more than 8 m/s, and (b) the flow rate, averaged over the cross-section, of the reaction mixture in this section of the reaction space (i.e. in the region of a conversion of the amine groups into isocyanate groups of from 4% to 80%) is always below the flow rate averaged over the cross-section at the start of this section.

BRIEF DESCRIPTION OF THE DRAWING

FIG. 1 is a graph of the flow fate averaged over the cross-section of the reactor used in Examples 2 and 3.

DETAILED DESCRIPTION OF THE PRESENT INVENTION

It has been found that preparation of aromatic isocyanates by phosgenation of the corresponding amines with phosgene in the gas phase is possible in reactors with a reaction space which is essentially rotationally symmetric to the direction of flow if (a) the flow rate, averaged over the cross-section, of the reaction mixture along the axis of the essentially rotationally symmetric reaction space in the section of the reaction space in which the conversion of the amine groups into isocyanate groups is between 4 and 80% is not more than 8 m/s, and (b) the flow rate, averaged over the cross-section, of the reaction mixture in this section of the reaction space (i.e. in the region of a conversion of the amine groups into isocyanate groups of from 4% to 80%) is always below the flow rate averaged over the cross-section at the start of this section. The benefits of using the reactors according to the invention in combination with the reaction conditions according to the invention are particularly surprising because in spite of the absence of stabilization of the flow of the reaction mixture by a high flow rate and in spite of the absence of stabilization of the flow of the reaction mixture by a constant or accelerating flow rate of the reaction mixture, high yields are achieved in the reaction of aromatic amines with phosgene to give the corresponding aromatic isocyanates with at the same time long service lives of the reactors. This was not foreseen. The use of reactors having reaction spaces which are essentially rotationally symmetric to the direction of flow with the reaction conditions required in the present invention leads to a short construction length of the reactors which is particularly advantageous for a conversion of the process to an industrial scale.

The present invention therefore provides a process for the preparation of aromatic isocyanates by reaction of one or more aromatic primary amines with phosgene in the gas phase in which phosgene and the primary aromatic amine(s) are reacted above the boiling temperature of the amine(s) in a reactor having a reaction space which is essentially rotationally symmetric to the direction of flow. In this process,
  a) the flow rate, averaged over the cross-section, of the reaction mixture along the axis of the essentially rotationally symmetric reaction space in the section of the reaction space in which the conversion of the amine groups into isocyanate groups is between 4 and 80% is not more than 8 m/s, preferably from 0.5 to 8 m/s, most preferably from, 1 to 6.5 m/s, and
  b) the flow rate, averaged over the cross-section, of the reaction mixture along the axis of the essentially rotationally symmetric reaction space in the section of the reaction space in which the conversion of the amine groups into isocyanate groups is between 4 and 80% is always below the flow rate averaged over the cross-section at the start of this section.

The rate conditions specified in a) and b) for the region in which the conversion of the amine groups into isocyanate groups is from 4% to 80% (i.e., the region of the reaction space in which the conversion of the amine groups into isocyanate groups is in the range of from 4% to 80%) are important because only when a minimum conversion of the amine groups into isocyanate groups is reached do the enthalpy of the reaction and the increase in the volume of the reaction mixture due to the reaction have a significant influence on the flow in the reaction space. The flow in the reaction space is then generated by the essential characteristic values of the reaction. This is largely the case from a conversion of the amine groups into isocyanate groups of 4%, preferably even already at lower conversions. The process of the present invention is, of course, also advantageously operated in the same manner from the stated lower limit of 4% of the conversion of the amine groups into isocyanate groups through the entire range of up to 80% conversion of the amine groups into isocyanate groups.

"Aromatic isocyanates" in the context of the present invention are those which have at least one isocyanate group bonded to at least one aromatic ring system.

In the process of the present invention, the reaction of phosgene with aromatic primary amine(s) is carried out in the gas phase. Reaction in the gas phase means that the reaction conditions are chosen so that the educts, reaction intermediate products and products and, where appropriate, inert compounds metered in during the course of the reaction remain predominantly in the gas phase during passage through the reaction space, in particular to the extent of ≥95 wt. %, preferably to the extent of ≥98 wt. %, more preferably ≥99 wt. %, even more preferably ≥99.8 wt. % and most preferably ≥99.9 wt. %, in each case based on the weight of the reaction mixture. Intermediate products in this context are, for example, monoamino-monocarbamoyl chlorides, dicarbamoyl chlorides, monoamino-monoisocyanates and monoisocyanate-monocarbamoyl chlorides formed if diamines are employed, and the hydrochlorides of the particular amino compounds.

The reaction of phosgene with aromatic primary amines in accordance with the present invention is carried out in at least one reaction space, which is in general arranged in a reactor. The "reaction space" is understood as meaning the space in which the reaction of the educts and intermediate products takes place. The "reactor" is understood as meaning the technical device which includes the reaction space. The educts, optionally diluted with inert gases, are in general fed to the reaction space via at least one mixing device.

Preferably, the reaction space employed in the process of the present invention includes in the front region at least one mixing space in which the mixing of the phosgene and amine components entering in gaseous form, optionally mixed with one or more inert substances, predominantly takes place. As a rule, this mixing is accompanied by the start of the reaction. For differentiation purposes, the region of the reaction space in which the amine groups are converted into isocyanate groups to a degree which is less than 4% is called the "mixing space".

"Conversion of the amine groups into isocyanate groups" in the context of the present invention is to be understood as meaning the consumption of amine groups to form isocyanate groups. This conversion can be monitored directly by taking samples along the reactor and immediately analyzing the sample taken from the particular segment of the reaction space. This analysis may be conducted by an FT-IR technique with evaluation of the NCO band in the region of 2270 cm$^{-1}$ and then relating the isocyanate group concentration measured to the isocyanate group concentration to be expected at a complete conversion of the amine groups into isocyanate groups. Preferably, the samples are taken via a probe which can be displaced along the cross-section of the reaction space so that the measurement gas removed continuously from the reaction space then flows as far as possible without a delay through the measurement cell of an FT-IR instrument. Such probes and techniques are known to those skilled in the art. The percent conversion of the amine groups into isocyanate groups is therefore based on the ratio of the concentration of the isocyanate groups present to the theoretically possible concentration of isocyanate groups if all the amine groups were converted into isocyanate groups.

In the context of the present invention, the "flow rate, averaged over the cross-section, of the reaction mixture along the axis of the reaction space which is essentially rotationally symmetric to the direction of flow" is to be understood as meaning the quotient of the volume stream integrated over the flow cross-sectional area divided by the flow cross-sectional area.

"Rotationally symmetric" in the context of the present invention and in accordance with prior art teaching (See, e.g., WO2007/028 751 A1, p. 3, 1. 28 et seq.) means that a body or space, here the reaction space, has a rotational symmetry when rotated about the axis of rotation. This can be, for example, a dihydric axis of rotation $C_2$, a trigyric $C_3$ or a tetrahydric axis of rotation $C_4$, or preferably complete rotational symmetry ($C_\infty$). Thus, for example, an area bordered by an ellipse has a dihydric axis of rotation. As a further example, an area bordered by a circle has complete rotational symmetry.

Reaction spaces which have flow cross-sections which are oval or composed of any desired closed planar polygons are not preferred, but are in principle also possible.

"Reaction space which is essentially rotationally symmetric to the direction of flow" in the context of the present invention means that from its properties, the essentially rotationally symmetric reaction space behaves quite predominantly like a rotationally symmetric reaction space. Preferably, in this context, the cross-sectional areas of the reaction space deviate, e.g. due to production-related tolerances, less than 10%, more preferably less than 5%, most preferably less than 2%, from the underlying mathematical rotational symmetry. Preferably, the essentially rotationally symmetric reaction space is in fact rotationally symmetric. Most preferably, a tube reactor having a flowed-through cross-sectional area which widens, remains constant and/or decreases, optionally also only in sections, in the direction of flow is employed.

In a preferred embodiment of the present invention, aromatic isocyanates are prepared by reaction of one or more aromatic primary amines with phosgene in the gas phase. In this preferred process, phosgene and the primary aromatic amine(s) are reacted above the boiling temperature of the amine(s) in a reactor having a reaction space which is essentially rotationally symmetric to the direction of flow in which
   a) the flow rate, averaged over the cross-section, of the reaction mixture along the axis of the essentially rotationally symmetric reaction space in the section of the reaction space in which the conversion of the amine groups into isocyanate groups is between 4 and 90%, more preferably between 4 and 99%, most preferably between 4 and 99.5%, is not more than 8 m/s, preferably from 0.5 to 8 m/s, most preferably from 1 to 6.5 m/s, and
   b) the flow rate, averaged over the cross-section, of the reaction mixture along the axis of the essentially rotationally symmetric reaction space in the section of the reaction space in which the conversion of the amine groups into isocyanate groups is between 4 and 90%, more preferably between 4 and 99%, most preferably between 4 and 99.5%, is always below the flow rate averaged over the cross-section at the start of this section.

Preferably, the flow rate, averaged over the cross-section, of the reaction mixture is also already a maximum of 8 m/s in the region of the conversion of the amine groups into isocyanate groups of from 0 to 4%. Likewise, the flow rate, averaged over the cross-section, of the reaction mixture is preferably also not more than 8 m/s in the region of the conversion of the amine groups into isocyanate groups of >99.5%.

In another preferred embodiment of the process of the present invention, the lowering of the flow rate, averaged over the cross-section, of the reaction mixture along the axis of the rotationally symmetric reaction space is achieved by at least one widening, preferably a conical widening, of the flowed-through cross-sectional area of the reaction space. Preferably, the reaction space always has, in the expanding region, an expanding half-angle, i.e., the angle between the reaction space wall and reaction space axis is generally ≤6°, preferably ≤3.5°, most preferably ≤2°.

In a further preferred embodiment of the process of the present invention, the reactor has, after the reaction space in which, after mixing of the educts, a conversion of the amine groups into isocyanate groups of 80%, preferably 90%, more preferably 99%, most preferably 99.5% is reached, a rotationally symmetric reaction space with a constant and/or widened flowed-through cross-sectional area.

In yet another preferred embodiment of the present invention, the reaction space downstream of the section in which, after mixing of the educts a conversion of the amine groups into isocyanate groups of 80%, preferably 90%, more preferably 99%, most preferably 99.5% is reached has at least one zone in which at least one liquid is injected for discontinuation of the reaction of the amine with the phosgene to give the isocyanate.

In this regard, the overall reaction of the amine groups with the phosgene to give isocyanate groups includes not only the consumption of the amine employed, but also the reaction of the intermediate products formed during consumption of the amine employed to give me isocyanate. Examples of possible intermediate products are monoamine-monocarbamoyl chlorides, dicarbamoyl chlorides, monoamine-monoisocyanates and monoisocyanate-monocarbamoyl chlorides if a diamine is employed, and the hydrochlorides of the particular amino compounds. In the conversion of a gas phase phosgenation to an industrial scale, the reaction conditions necessary for the reaction of the intermediate products to give the isocyanate (for example, the reaction times necessary for the reaction) determine to a considerable extent the design of the industrial apparatuses.

Primary aromatic amines can be used in the process of the present invention. Preferably, primary aromatic amines which can be converted into the gas phase essentially without decomposition are employed.

Examples of preferred aromatic amines are toluenediamine (TDA), in particular 2,4-TDA and 2,6-TDA and mixtures, thereof, diaminobenzene, naphthyldiamine (NDA); and 2,2'-, 2,4'- or 4,4'-methylenediphenyldiamine (MDA) and isomer mixtures thereof. Toluenediamine (TPA), in particular 2,4-TDA and 2,6-TDA and mixtures thereof, is particularly preferred.

Before carrying out the process of the present invention, the starting amine(s) as a rule is/are vaporized and heated to 200° C. to 600° C., preferably 200° C. to 500° C., most preferably 250° C. to 450° C., and are optionally fed to the reaction space in a form diluted with an inert gas such as $N_2$, He or Ar or with the vapors of an inert solvent (e.g., aromatic hydrocarbons, optionally with halogen substitution, such as chlorobenzene or o-dichlorobenzene).

The vaporization of the starting amine(s) can be carried out in any of the known vaporization apparatuses. Vaporization systems which are preferred are those in which a small work content is led with a high circulating output over a falling film evaporator, and to minimize the exposure of the starting amines to heat the vaporization process, is optionally assisted with feeding in of inert gas and/or vapors of an inert solvent.

In a particularly preferred embodiment of the present invention, vaporization systems in which a small work content is circulated over at least one micro-heat exchanger or micro-evaporator are employed. The use of appropriate heat exchangers for vaporization of amines is disclosed, e.g., in EP-A-1 754 698. The apparatuses disclosed in paragraphs [0007] to [0008] and [0017] to [0039] of EP-A-1 754 689 are preferably employed in the process of the present invention.

The vaporous amines may still contain contents of non-vaporized droplets of amines (aerosol). However, the vaporous amines preferably contain essentially no droplets of non-vaporized amines, i.e., not more than 0.5 wt. % of the amine, most preferably not more than 0.05 wt. % of the amine, based on the total weight of amine, is present in the form of non-vaporized droplets with the remainder of the amine being present in vaporous form. Most preferably, the vaporous amines contain no droplets of non-vaporized amines. Preferably, after the vaporization the vaporous amine, optionally diluted with inert gases or inert solvent vapors, is brought to the desired use temperature via an after-heater.

The vaporization and superheating of the starting amine(s) furthermore is preferably carried out in several stages in order to avoid non-vaporized droplets in the vaporous amine stream. Multi-stage vaporization and superheating steps in which droplet separators are incorporated between the vaporization and superheating systems and/or the vaporization apparatuses also have the function of a droplet separator and are particularly preferred. Suitable droplet separators are described, e.g., in "Droplet Separation", A. Bürkholz, VCH Verlagsgesellschaft, Weinheim—New York—Basel—Cambridge, 1989. Droplet separators which cause a low pressure loss are particularly preferred. It is especially preferred that the vaporized amine be brought to the desired use temperature via at least one after-heater, which also functions as a droplet separator. Most preferably, this after-heater has a liquid drain in order to ensure constant emptying of the separator. After leaving the last superheater in the direction of flow, the vaporous amine which has been preheated to its intended temperature is fed with an average dwell time of from preferably 0.01 to 60 s, more preferably from 0.01 to 30 s, most preferably from 0.01-15 s to the reactor or the mixing device thereof for reaction. The risk of renewed formation of droplets is counteracted via technical measures, e.g., an adequate insulation to avoid losses by radiation. The reactor running time is increased significantly by generation of an essentially droplet-free vaporous stream of starting amine before entry into the reactor.

In a preferred embodiment, the vaporous amine stream is fed to the reactor or at least one mixing device therein with a low pressure loss without a regulating device, but a regulated feed is likewise possible. A division of the amine stream into several smaller streams, which are then fed as described, e.g., in EP-A-1 449 826 in paragraphs [0019] to [0022] to a reaction space or, as described, e.g., in WO 2008/055898 page 8/line 25 to page 15/line 31 and in particular page 23/lines 19-31, to several mixing devices, is also possible. In the case of a split in the vaporous amine stream, the feeding of the smaller amine streams preferably also takes place with a low pressure loss without additional regulating devices. However, separately regulated feeding of the smaller streams is also possible.

In the process of the present invention, it is advantageous to employ phosgene in excess with respect to the amine groups to be reacted. Preferably, a molar, ratio of phosgene to amine groups of from 1.1:1 to 20:1, preferably from 1.2:1 to 5:1 is present. The phosgene is also heated to a temperature of from 200° C. to 600° C. and optionally fed to the reaction space in dilute form with an inert gas, such as $N_2$, He or Ar, or with the vapors of an inert solvent (e.g., aromatic hydrocarbons, without or with halogen substitution, such as chlorobenzene or o-dichlorobenzene).

In a preferred embodiment, regulated feeding of the phosgene stream to the reactor or at least one mixing device therein takes place. However, feeding with a low pressure loss without a regulating device is likewise possible. A division of the phosgene stream into several part streams, which are then fed as described, e.g., in WO 2008/055898 page 8/line 25 to page 15/line 31 and in particular page 23/lines 19-31, to several mixing devices of a reactor, is also possible. Feeding of the part streams to several reactors is also possible. In the case of a split in the phosgene stream, separately regulated feeding of the phosgene part streams preferably takes place.

In the process of the present invention, separately heated reaction components are introduced via at least one mixing device into at least one reaction space, mixed, and reacted taking account of suitable reaction times under a preferably adiabatic reaction procedure. The isocyanate thus produced is then condensed by cooling the gas stream, the cooling taking place to a temperature above the decomposition temperature of the corresponding carbamic acid chloride (e.g., to a temperature above the decomposition temperature of toluenemonoisocyanate monocarbamic acid chloride and/or toluenedicarbamatic acid chloride in the case of TDA).

The necessary dwell time for reaction of the amine groups with the phosgene to give isocyanate groups is between 0.05 and 15 seconds, depending on the nature of the amine employed, the start temperature, the adiabatic increase in temperature in the reaction space, the molar ratio of amine to phosgene, any dilution of the reaction components with inert gases and the reaction pressure chosen.

If the minimum dwell time determined to be necessary for the complete reaction for the particular system (amine employed, start temperature, adiabatic increase in temperature, molar ratio of the reactants, dilution gas, reaction pressure) is exceeded by less than 20%, preferably less than 10%, the formation of secondary reaction products, such as isocyanurates and carbodiimides, can be largely avoided.

Within this contact time spectrum, which is very narrow for chemical reactions, both mixing of the reaction components which is as homogeneous as possible and the further reaction must take place. In this context, the further reaction preferably takes place without back-mixing, which would have the effect of broadening of the contact period of time and therefore increased formation of undesirable by-products and secondary products.

In practicing the process of the present invention, a deviation from the average contact time can take place due to the time necessary for mixing of the reaction components. Methods for implementing short mixing times are known in principle. Mixing units or mixing spaces with moving or static mixing devices or nozzles, for example, are suitable. The use of static mixers in mixing spaces, such as is described in EP-A-1 362 847, EP-A-1 526 129 or EP-A-1 555 258, is preferred. The apparatuses disclosed in paragraphs [0008] to [0014] and [0023] to [0026] of EP-A-1 362 847, those disclosed in paragraphs [0008] to [0013] and [0022] to [0026] of EP-A-1 526 129 or those disclosed in paragraphs [0007] and [0024] to [0025] of EP-A-1 555 258 are preferably employed in the process of the present invention.

Reactors with essentially rotationally symmetric reaction spaces in which the gaseous educts, optionally diluted with inert substances, are fed to the at least one mixing space in accordance with the jet mixer principle (Chemie-Ing. Techn. 44 (1972) p. 1055, FIG. 10) are most preferably employed. In this context, the substance streams preferably enter into the at least one mixing space of the reactors with a speed ratio of from 2 to 20, preferably from 3 to 15, most preferably from 4 to 12. Preferably, the amine, optionally diluted with one or more inert substances, is fed with the higher flow rate to the at least one mixing space of the reactor(s).

Preferably, neither the reaction space nor any mixing units or mixing spaces have heating surfaces or cooling surfaces. Heating surfaces can give rise to exposure to heat causing secondary reactions, such as isocyanurate or carbodiimide formation. Cooling surfaces can give rise to condensation and cause deposits. It is preferred that the components be reacted adiabatically, apart from any losses by radiation and conduction. In this context, the adiabatic increase in temperature in the mixing unit and reactor or reactor is established solely via the temperatures, compositions and relative meterings of the educt streams and the dwell time in the mixing unit(s) and the reactor(s).

After the phosgenation reaction has taken place in the reaction space, the gaseous reaction mixture, which preferably includes at least an isocyanate, phosgene and hydrogen chloride, is freed from the isocyanate formed. This can be carried out, for example, by subjecting the mixture leaving the reaction space continuously to a condensation in an inert solvent after leaving the reaction space, as has already been recommended for other gas phase phosgenations (EP-A-0 749 958).

Preferably, however, the condensation is carried out by a procedure in which the reaction space employed in the process of the present invention has at least one zone into which one or more suitable streams of liquid ("quench liquids") are sprayed for discontinuation of the reaction of the amine(s) and the phosgene to give the corresponding isocyanates. By this means, as described in EP-A-1 403 248, rapid cooling of the gas mixtures can be carried out without the use of cold surfaces.

In a particularly preferred form of the process of the present invention, the at least one zone (cooling zone) is integrated into a quenching stage, such as has been disclosed in EP-A-1 403 248. In one of the most preferred embodiments of the present invention, several cooling zones are employed, and these at least two cooling zones are integrated and operated with a quenching stage. The construction and operation of such cooling zones are disclosed in EP-A-1 935 875.

Instead of the integrated combination of the at least one cooling zone of a reactor with a quenching stage, the corresponding integrated combination of the cooling zones of several reactors with a quenching stage is likewise possible. Preferably, however, the integrated combination of a reactor with at least one cooling zone having a quenching stage is preferred.

In a preferred embodiment of the process of the present invention, the throughput capacity of the reactor employed under the required reaction conditions is <1 t of amine/h, preferably from 2 to 50 t of amine/h, most preferably from 2 to 12 t of amine/h. These values most preferably apply to toluenediamine. In this context, throughput capacity means that the stated throughput capacity of amine per h can be reacted in the reactor.

Regardless of the nature of the cooling method chosen, the temperature of the at least one cooling zone is preferably selected so that it is above the decomposition temperature of the carbamoyl chloride corresponding to the isocyanate, and the isocyanate and optionally the solvent (co-used as a diluent in the amine vapor stream and/or phosgene stream) condense to the greatest extent or dissolve in the solvent to the greatest extent, while excess phosgene, hydrogen chloride and inert gas (optionally co-used as a diluent) pass through the condensation or quenching stage to the greatest extent without being condensed or dissolved. Solvents kept at a temperature of from 80 to 200° C., preferably 80 to 180° C., such as chlorobenzene and/or dichlorobenzene, or isocyanate or mixtures of the isocyanate with chlorobenzene and/or dichlorobenzene kept in these temperature ranges are particularly suitable for selective isolation of the isocyanate from the gaseous reaction mixture. On the basis of the physical data at a given temperature, pressure and composition, the person skilled in the art can easily determine what weight content of the isocyanate condenses in the quenching or passes through without being condensed. It is likewise easy to determine what weight content of the excess phosgene, hydrogen chloride and inert gases optionally used as a diluent passes through the quenching without being condensed or dissolved in the quenching liquid.

Generation of the flow of the gaseous reaction mixture as a flow through the reaction space without substantial backmixing, which is preferred for the process of the present invention, is ensured by a pressure gradient over the reaction space. The pressure gradient preferably exists between the educt feed lines before the mixing and the exit from the condensation or quenching stage. Preferably, the absolute pressure in the educt feed lines before the mixing is 200 to 3,000 mbar and after the condensation or quenching stage is from 150 to 2,500 mbar. However, it is essential to maintain a pressure difference of preferably at least 50 mbar from the educt feed lines via the reaction space to after the condensation or quenching stage for the purpose of ensuring directed flow and a good mixing of the educts.

The gas mixture leaving the condensation or quenching stage is preferably freed from residual isocyanate in a downstream gas wash with a suitable wash liquid. This gas mixture is preferably then freed from excess phosgene in any manner known to those skilled in the art. This can be carried out by means of a cold trap, absorption in an inert solvent (e.g., chlorobenzene or dichlorobenzene) or by adsorption and hydrolysis on active charcoal. The hydrogen chloride gas passing, through the phosgene recovery stage can be recycled in any manner known to be suitable for recovery of the chlorine required for the synthesis of phosgene. The wash liquid obtained after its use for the gas wash is then preferably at least partly employed as the quench liquid for cooling the gas mixture in the corresponding zone of the reaction space.

The isocyanates are subsequently preferably prepared in a pure form by working up the solutions or mixtures from the condensation or quenching stage by distillation.

Having thus described the invention in general terms, the following examples are given to illustrate the invention.

EXAMPLES

The degree of conversion of the amine groups into isocyanate groups can be determined by taking samples along the reactors employed and immediately analyzing the sample taken from the particular segment of the reaction space by any of the known FT-IR techniques. Such techniques evaluate the NCO band in the region of 2270 cm$^{-1}$. In this context, the samples are taken in the segments via a probe which can be displaced along the cross-section of the segment of the reaction space. The measurement gas removed continuously from the reaction space then flows through the measurement cell of an FT-IR device employed in accordance with known techniques. For determination of the isocyanate group concentration at the measurement point, the probe is displaced radially over the cross-section of the reaction space at the measurement point, in order to obtain corresponding measurements of the local isocyanate group concentration at several locations. An isocyanate group concentration averaged over the cross-section is calculated from the isocyanate group concentration profile obtained in this way, and the conversion of the amine groups into isocyanate groups at the measurement point is subsequently determined as the quotient of the isocyanate group concentration averaged over the cross-section divided by the isocyanate group concentration resulting in the case of complete conversion of the amine groups into isocyanate groups.

The flow rate averaged over the cross-section can be determined by using a Prandtl tube to measure the dynamic pressure, as is described, e.g., in W. Bohl, "Technische Strömungslehre", 5th revised edition, Vogel-Buchverlag, Würzburg, 1982, p. 217 et seq. The local pressure measured with the aid of the Prandtl tube is converted into a local flow rate by estimating the local gas density. For determination of the flow rate averaged over the cross-section at the measurement point, the Prandtl tube is displaced radially over the cross-section of the reaction space at the measurement point, in order to obtain corresponding measurements of the local rate at several locations. From the rate profile obtained in this way, the gas volume stream is determined by a numerical integration of the gas volume stream. The flow rate averaged over the cross-section is subsequently determined as the quotient of the volume stream integrated over the flow cross-sectional area divided by the flow cross-sectional area.

The examples described in the following are based on a flow simulation on the basis of solution of the Navief-Stokes equations, as is described in its essential features in A. Paschedag, "CFD in der Verfahrenstechnik", Wiley-VCH-Verlag, Weinheim, 2004. Kinetic data of the reaction of 2,4-TDA with phosgene were employed in this base model.

Example 1

Comparative 2,500 kg/h of 2,4-toluenediamine (TDA for short) were vaporized and fed in gaseous form at a temperature of 410° C. to a cylindrical rube reactor (diameter 380 nm) via a nozzle (diameter 70 mm) arranged on the reactor axis. At the same time, in parallel with this 8,097 kg/h of gaseous phosgene were heated to 390° C. and likewise fed to the tube reactor at the annular space left free by the one nozzle. The streams were mixed in the tube reactor under an operating pressure of 1,400 mbar abs., the reaction of the amine groups to give isocyanate groups started at the same time. 630 mm downstream of the nozzle mouth, a conversion of the amine groups into isocyanate groups of 12% was reached, and the flow rate averaged over the cross-section started to increase significantly there due to the volume expansion as a result of reaction stoichiometry and exothermicity. It was found that the flow rate averaged over the cross-section was always higher from a conversion of the amine groups into isocyanate groups of 12% after a length of 630 mm from the nozzle mouth, than at the conversion of the amine groups into isocyanate groups of 12% at the length of 630 mm (9.9 m/s there). A final value of 16.3 m/s was reached at the reactor exit. At a 2,4-toluenediisocyanate yield of >99.5%, a minimum reaction space length from the nozzle mouth of 19.9 m was required before the reaction of the 2,4-toluenediamine and its secondary products with the phosgene-were completed to the greatest extent.

Example 2

Comparative 2,500 kg/h of 2,4-toluenediamine (TDA for short) were vaporized and fed in gaseous form at a temperature of 410° C. to a cylindrical tube reactor (diameter 600 nm) via a nozzle (diameter 110 mm) arranged on the reactor axis. At the same time, in parallel with this 8,097 kg/h of gaseous phosgene were heated to 390° C. and likewise fed to the tube reactor at the annular space left free by the one nozzle. The streams were mixed in the tube reactor under an operating pressure of 1,400 mbar abs. The reaction of the amine groups to give isocyanate groups started at the same time. 350 mm downstream of the nozzle mouth, a conversion of the amine groups into isocyanate groups of 4% was reached, and the flow rate averaged over the cross-section started to increase significantly there due to the volume expansion as a result of reaction stoichiometry and exothermicity. The course of the flow rate averaged over the cross-section with respect to the length of the tube reactor is shown in FIG. 1. It was found that the flow rate averaged over the cross-section was always higher from a conversion of the amine groups into isocyanate groups of 4% after a length of 350 mm from the nozzle mouth, than at the conversion of the amine groups into isocyanate groups of 4% at the length of 350 mm. At a 2,4-toluene-diisocyanate yield of >99.5%, a minimum reaction space length from the nozzle mouth of 8 m is required before the reaction of the 2,4-toluenediamine and its secondary products with the phosgene were completed to the greatest extent.

Example 3

According to the Invention 2,500 kg/h of 2,4-toluenediamine (TDA for short) were vaporized and fed in gaseous form at a temperature of 410° C. to a cylindrical-conical tube reactor via a nozzle (diameter 110 mm) arranged on the reactor axis. At the same time, in parallel with this 8,097 kg/h of gaseous phosgene were heated to 390° C. and likewise fed to the tube reactor at the annular space left free by the one nozzle. The reactor had a diameter of 600 mm in the region of the educt feed. This diameter was retained to an axial position 350 mm downstream of the nozzle mouth, and thereafter a section with a conical expansion (expanding half-angle, i.e., angle between the reactor wall and reactor axis equal to 3.5°) followed. The streams were mixed in the tube reactor under an operating pressure of 1,400 mbar abs. The reaction of the amine groups to give isocyanate groups started at the same time. 350 mm downstream of the nozzle mouth a conversion of the amine groups into isocyanate groups of 4% was reached. The gas volume stream started to increase significantly due to the stoichiometry and the reaction enthalpy, but as a result of the increasing flow cross-section, at no location lying downstream did the flow rate averaged over the cross-section exceed the starting rate averaged over the cross-section at the location of the stated conversion of the amine groups into isocyanate groups of 4%, i.e. at a length of the tube, reactor of 350 mm. The course of the flow rate averaged over the cross-section with respect to the length of the tube reactor is shown in FIG. 1. It was found that the flow rate averaged over the cross-section was always lower from a conversion of the amine groups into isocyanate groups of 4%, i.e. after a length of 350 mm from the nozzle mouth, than at the conversion of the amine groups into isocyanate groups of 4%, i.e. at the length of 350 mm. At a 2,4-toluene-diisocyanate yield of >99.5%, a minimum reaction space length from the nozzle mouth of only 4.2 m was required before the reaction of the 2,4-toluenediamine and its secondary products with the phosgene had been to the greatest extent completely concluded.

FIG. 1 shows the course of the flow rate averaged over the cross-section for Examples 2 and 3. In this context, the position of the nozzle mouth was in each case at a length of the tube reactor x=0 m. The flow rate v averaged over the cross-section is stated in m/s. E2 and E3 identify Example 2 and Example 3.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A process for the production of an aromatic isocyanate comprising
  a) combining at least one aromatic primary amine with phosgene in the gas phase at a temperature above the boiling temperature of the amine to form a reaction mixture,
  b) reacting the reaction mixture in a reactor comprising a reaction space which is essentially rotationally symmetric to direction of flow of the reaction mixture in which
    (i) flow rate, averaged over cross-section of the reactor, of the reaction mixture along the axis of the essentially rotationally symmetric reaction space in a section of the reaction space in which conversion of amine groups in the amine into isocyanate groups is from 4 to 80% complete is not more than 8 m/s and
    (ii) the flow rate, averaged over the cross-section, of the reaction mixture along the axis of the essentially rotationally symmetric reaction space in the section of the reaction space in which the conversion of the amine groups into isocyanate groups is between 4 and 80% is always lower than a flow rate averaged over the cross-section at the start of this section, wherein the reaction space in the section of the reaction space in which the conversion of the arsine groups into isocyanate groups is between 4 and 80% has a widened flowed-through cross-sectional area of the reaction space.

2. The process of claim 1 wherein the conical widening has an expanding haft-angle of ≤6°.

3. The process of claim 1 wherein the conical widening has an expanding half-angle of ≤3.5°.

4. The process of claim 1 wherein the conical widening has an expanding half-angle of ≤2°.

5. The process of claim 1 in which after the section of the reaction space in which the conversion of the amine groups into isocyanate groups is between 4 and 80% the reactor has an essentially rotationally symmetric reaction space with a constant and/or widening flowed-through cross-sectional area.

6. The process of claim 1 in which the mixing and the reacting are carried out isothermally or at least partly adiabatically.

7. The process of claim in which the essentially rotationally symmetric reaction space has at least one zone in which at least one liquid is injected for discontinuation of the reaction.

8. The process of claim 7 in which the cross-sectional area of the at least one zone in which at least one liquid is injected for discontinuation of the reaction is equally as large or larger than the cross-sectional area of the reaction space in which the reaction takes place.

9. The process of claim 1 in which the phosgene and the amine are fed to the reaction space in gaseous form using a jet mixer.

10. The process of claim 1 in which an amine-containing or phosgene-containing stream fed into the reaction space is fed to the reaction space at an average flow rate ratio of from 2 to 12.

11. The process of claim 9 in which the stream containing the amine enters into the reaction space at a higher average flow rate than the stream containing the phosgene.

12. The process of claim 1 in which the amine is a diamine.

13. The process of claim 1 in which the amine is 2,4-toluenediamine, 2,6-toluenediamine or a mixture thereof.

14. The process of claim 1 in which the reactor has a throughput capacity of >1 t of amines/h.

\* \* \* \* \*